US006096933A

United States Patent [19]
Cheung et al.

[11] Patent Number: 6,096,933
[45] Date of Patent: Aug. 1, 2000

[54] HYDROCARBON HYDROGENATION AND CATALYST THEREFOR

[75] Inventors: Tin-Tack Peter Cheung; Marvin M. Johnson, both of Bartlesville, Okla.

[73] Assignee: Phillips Petroleum Company, Bartlesville, Okla.

[21] Appl. No.: 09/039,041

[22] Filed: Mar. 13, 1998

Related U.S. Application Data

[63] Continuation-in-part of application No. 08/867,872, Jun. 4, 1997, Pat. No. 5,866,735, which is a continuation-in-part of application No. 08/595,326, Feb. 1, 1996, abandoned.

[51] Int. Cl.[7] ............... C07C 5/03; C07C 7/163
[52] U.S. Cl. ............ 585/260; 585/261; 585/262; 585/277; 502/330; 502/333; 502/339
[58] Field of Search .................. 585/250, 259, 585/261, 271, 262, 273, 275, 277, 260; 502/330, 333, 339

[56] References Cited

U.S. PATENT DOCUMENTS

| | | | |
|---|---|---|---|
| 3,878,260 | 4/1975 | Kunugi et al. | 260/680 E |
| 3,932,548 | 1/1976 | Rausch | 260/668 D |
| 4,113,970 | 9/1978 | Tanabe et al. | 560/244 |
| 4,341,912 | 7/1982 | Takahashi et al. | 585/443 |
| 4,429,155 | 1/1984 | Goetz et al. | 564/402 |
| 4,431,750 | 2/1984 | McGinnis et al. | 502/329 |
| 4,435,607 | 3/1984 | Imai | 585/443 |
| 4,484,015 | 11/1984 | Johnson et al. | 585/262 |
| 4,538,009 | 8/1985 | Goetz et al. | 568/799 |
| 4,717,781 | 1/1988 | Imai et al. | 585/441 |
| 5,057,206 | 10/1991 | Engel et al. | 208/143 |
| 5,475,173 | 12/1995 | Cheung et al. | 585/259 |
| 5,488,024 | 1/1996 | Cheung et al. | 502/325 |
| 5,489,565 | 2/1996 | Cheung et al. | 502/325 |
| 5,583,274 | 12/1996 | Cheung et al. | 585/261 |
| 5,585,318 | 12/1996 | Johnson et al. | 502/330 |
| 5,587,348 | 12/1996 | Brown et al. | 502/230 |
| 5,698,752 | 12/1997 | Brown et al. | 585/260 |

*Primary Examiner*—Bekir L. Yildirim
*Attorney, Agent, or Firm*—Richmond, Hitchcock, Fish & Dollar

[57] ABSTRACT

A supported hydrogenation catalyst composition is disclosed which comprises a palladium component, at least one alkali metal iodide such as, for example, potassium iodide, and an inorganic support material such as alumina. The palladium component is concentrated in an area within about 150 microns of the exterior surface of the composition. Also disclosed is a selective hydrogenation process in which diolefins and/or alkynes are hydrogenated with hydrogen to corresponding monoolefins.

66 Claims, 2 Drawing Sheets

HYDROCARBON HYDROGENATION AND CATALYST THEREFOR

This application is a continuation-in-part of application Ser. No. 08/867,872 filed Jun. 4, 1997, which is a continuation-in-part of application Ser. No. 08/595,326 filed Feb. 1, 1996, now abandoned.

FIELD OF THE INVENTION

This invention relates to a supported noble metal catalyst composition and to a process for selectively hydrogenating diolefins (alkadienes) and alkynes to monoolefins (alkenes) employing a supported noble metal catalyst composition.

BACKGROUND OF THE INVENTION

Catalysts comprising palladium and a support material are known catalysts for dienes and/or alkynes hydrogenation. Even though these catalysts are effective hydrogenation catalysts, some such catalysts tend to produce green oil by oligomerizing the alkynes and dienes. The green oil has 6 or more carbons per molecule and is not desirable in the production of an alkene such as, for example, ethylene because it fouls the catalyst and cuts the yield to alkene. Therefore, there is an ever present need for further improvements of a selective hydrogenation process to achieve enhanced selectivity to monoolefins, or increased catalyst life, or both. Accordingly, development of a modified supported palladium catalyst composition and its use in processes for the selective hydrogenation of diolefins (alkadienes) or alkynes to monoolefins (alkenes) would be a significant contribution to the art.

SUMMARY OF THE INVENTION

It is an object of this invention to provide an improved palladium-containing composition which can be useful as a catalyst in the selective hydrogenation of diolefins and/or alkynes to monoolefins. It is another object of this invention to employ this improved catalyst composition in the selective hydrogenation of diolefins or alkynes to monoolefins. It is also an object of this invention to employ this improved catalyst composition in the selective hydrogenation of alkadienes and alkynes to the corresponding alkenes. It is another object of this invention to employ this improved catalyst composition in the selective hydrogenation of cyclopentadienes to cyclopentene. It is a further object of this invention to employ this improved composition in the selective hydrogenation of dicyclopentadiene to at least one dihydrodicyclopentadiene. Other objects and advantages will be apparent from the detailed description and the appended claims.

In accordance with this invention, a catalyst composition is provided which comprises, consists essentially of, or consists of (a) at least one palladium-containing material selected from the group consisting of palladium metal and palladium oxides, (b) at least one alkali metal iodide and (c) at least one inorganic support material. The inorganic support can be a spinel, alumina, silica, titania, zirconia, aluminosilicates, or mixtures of two or more thereof.

In accordance with a second embodiment of this invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition, under a condition sufficient to effect a selective hydrogenation of the highly unsaturated hydrocarbon. The catalyst composition can be the same as the composition disclosed in the first embodiment of this invention.

DETAILED DESCRIPTION OF THE INVENTION

As used in the present invention, the term "fluid" denotes gas, liquid, vapor, or combinations thereof. The term "saturated hydrocarbon" is referred to as any hydrocarbon which can be converted to an unsaturated hydrocarbon such as an olefinic compound by a thermal cracking process. An "unsaturated hydrocarbon" as used in this application is a hydrocarbon having at least one double bond between carbon atoms in the molecule. Generally, examples of saturated hydrocarbons include, but are not limited to, ethane, propane, butanes, pentanes, hexanes, octanes, decanes, naphtha, and combinations of any two or more thereof. Examples of unsaturated hydrocarbons include, but are not limited to, monoolefins such as ethylene, propylene, butenes, pentenes, hexenes, octenes, and decenes; aromatic compounds such as naphthalene; alkynes such as acetylene, propyne, and butynes; diolefins such as propadiene, butadienes, pentadienes (including isoprene), hexadienes, octadienes, and decadienes; and combinations of two or more thereof. The term "highly unsaturated hydrocarbon" refers to a hydrocarbon which contains a triple bond or two or more double bonds in a molecule. The termn "less unsaturated hydrocarbon" refer to a hydrocarbon in which the triple bond in the highly unsaturated hydrocarbon is hydrogenated to a double bond or a hydrocarbon in which the number of double bonds is one less than that in the highly unsaturated hydrocarbon. The term "selective hydrogenation" is referred to as a hydrogenation process which converts a highly unsaturated hydrocarbon such as an alkyne or a diolefin to a less unsaturated hydrocarbon such as a monoolefin without hydrogenating the less unsaturated hydrocarbon to a saturated or a more saturated hydrocarbon such as alkane.

The composition of matter of this invention comprises, consists essentially of, or consists of component (a) palladium metal and/or at least one palladium oxide, component (b) at least one alkali metal iodide (preferably potassium iodide), and component (c) an inorganic support material selected from the group consisting of alumina, silica, titania, zirconia, aluminosilicates (clays and/or zeolites), zinc aluminate, zinc titanate, and combinations of two or more than two of these compounds, preferably alumina, more preferably alpha-alumina. Generally, the catalyst composition contains in the range of from about 0.01 weight-% palladium to about 2 weight-% palladium (Pd) (on a total catalyst composition weight basis) (preferably in the range of from about 0.05 weight-% Pd to about 1 weight-% Pd) and in the range of from about 0.02 weight-% alkali metal to about 10 weight-% alkali metal (on a total catalyst composition weight basis) (preferably in the range of from about 0.05 weight-% alkali metal to about 5 weight-% alkali metal) (preferably the alkali metal is potassium). The term "on a total catalyst composition weight basis" refers to the weight of the total catalyst composition. Thus, the weight-% of a component on a total catalyst composition weight basis is a percentage of the total catalyst composition weight.

The composition of this invention may be characterized as a "skin catalyst." The composition of this invention is preferably in the form of catalyst particles. The term "skin" refers to the exterior surface of the composition which can contain components of the composition. The skin can be any thickness as long as such thickness can promote the selective hydrogenation disclosed herein. Generally, the thickness of the skin can be in the range of from about 1 micron to about 1000 microns, preferably in the range of from about 5 microns to about 750 microns, more preferably in the range of from about 5 microns to about 500 microns, and most preferably in the range from 10 microns to 300 microns.

The catalyst hydrogenates more selectively when the skin is relatively thin (such as the most preferable skin thickness of 10 microns to 300 microns) than when then the skin is thicker (such as greater than 300 microns). Thus, there is a significant benefit, better selective hydrogenation, by preparing a composition with a thin skin, rather than a thick skin. Further, there is a significant benefit, better selective hydrogenation, by preparing a composition with a skin than a composition without a skin.

As used in the present invention, the term "skin catalyst" denotes that at least about 40 weight-% of the Pd (on a Pd weight basis, thus the term "40 weight-% of the Pd" refers to 40 percent of the about 0.01 weight-% Pd (on a total catalyst composition weight basis) to about 2 weight-% Pd (on a total catalyst composition weight basis)), preferably at least about 45 weight-% of the Pd (on a Pd weight basis), is concentrated preferably within about 50 microns of the exterior surface of the composition. At least about 50 weight-% of the Pd (on a Pd weight basis), preferably at least about 55 weight-% of the Pd (on a Pd weight basis), is concentrated preferably within about 100 microns of the exterior surface of the composition. At least about 60 weight-% of the Pd (on a Pd weight basis), preferably at least about 65 weight-% of the Pd (on a Pd weight basis), is concentrated preferably within about 150 microns of the exterior surface of the composition. Preferably about 80 weight-% of the Pd (on a Pd weight basis), most preferably about 90 weight-% of the Pd (on a Pd weight basis), is concentrated in the skin of the composition, preferably in an area within about 300 microns of the exterior surface of the composition. Various skin catalysts have been developed. See for example U.S. Pat. No. 4,404,124 and U.S. Pat. No. 4,484,015, disclosures of which are incorporated herein by reference.

One can use any suitable method to determine the concentration of the palladium in the skin of the composition. One technique currently favored is the electron microprobe which is well known to one skilled in the art. Another technique involves breaking open a representative sample of the composition (in catalyst particle form) and treating the catalyst particles with a dilute alcoholic solution of N,N-dimethyl-para-nitrosoaniline. The treating solution reacts with the palladium to give a red color which can be used to evaluate the distribution of the palladium. Another technique for measuring the concentration of the palladium in the skin of the composition involves breaking open a representative sample of catalyst particles followed by treatment with a reducing agent such as, for example hydrogen, to change the color of the skin to evaluate the distribution of the palladium.

The catalyst particles can be of any suitable shape (spherical, cylindrical, trilobal and the like), and are preferably either spherical pellets or cylindrical extrudates. The catalyst particles can be of any suitable dimension and particle size (diameter/length) and generally have a size in the range of from about 1 mm to about 10 mm. However, the advantages of the skin type catalyst are particularly notable for those particles having minimum dimensions of at least about 1 millimeter. A particularly suitable form of catalyst particle is one having dimensions in the range of from about 2 to about 6 millimeters. The catalyst particles can have any suitable surface area (measured by the BET method by Brunauer, Emmett and Teller employing $N_2$), and generally have a surface area in the range of from about 1 $m^2/g$ to about 200 $m^2/g$ (preferably in the range of from about 5 $m^2/g$ to about 100 $m^2/g$).

The catalyst particles can be prepared by any suitable means which results in the palladium concentrated in the exterior surface skin of the catalyst particles with the alkali metal iodide distributed in the skin or throughout the catalyst particles. Generally, the extent of penetration of the palladium into the skin of the catalyst particles can be controlled by adjustment of the acidity of the promoter-component containing solution with an acid such as, for example, hydrochloric acid. For example, if the promoter-component containing solution is palladium chloride ($PdCl_2$), hydrochloric acid should be added to such promoter-component containing solution to form a $PdCl_4^{-2}$ complex. Excess hydrochloric acid should be avoided. The promoter components (a) palladium metal and/or at least one palladium oxide, and (b) at least one alkali metal iodide (preferably potassium iodide) can be deposited onto and/or incorporated into the inorganic support material by any suitable means and in any suitable order.

It has been discovered that the combination of silver or silver-containing compounds with at least one alkali metal iodide (along with components (a) and (c)) results in a composition that is less effective in selective hydrogenation than the present inventive composition which does not contain a substantial concentration of silver or silver-containing compounds. Thus, it is preferred that the inventive composition contain no substantial concentration of silver or silver-containing compounds especially a substantial concentration such that there is a significant effect on the selective hydrogenation capabilities of the inventive catalyst composition. There is a significant effect on the selective hydrogenation capabilities of the inventive catalyst composition when 40 weight percent (on a total feed weight basis) fewer highly unsaturated hydrocarbons (preferably 30 weight percent fewer highly unsaturated hydrocarbons, most preferably 20 weight percent fewer highly unsaturated hydrocarbons) are converted to less unsaturated hydrocarbons during selective hydrogenation using the inventive catalyst composition than when a composition contains a substantial concentration of silver or silver-containing compounds. Most preferably, the inventive catalyst composition does not contain silver or silver-containing compounds.

While the palladium and alkali metal iodide containing composition (final catalyst composition) may be heated or calcined in an oxidizing gas atmosphere such as air at temperatures less than about 200° C., the final composition should not be heated or calcined in an oxidizing gas atmosphere at temperatures greater than about 200° C. Heating or calcining the final composition in an oxidizing gas atmosphere at temperatures greater than about 200° C. will result in the iodide being driven off in the form of gaseous iodine rendering the final composition unuseful for the selective hydrogenation disclosed herein.

For instance, the alkali metal iodide can be incorporated into the support material, by impregnation, followed by impregnation of the alkali metal iodide-containing support material with at least one Pd compound (such as $H_2PdCl_4$) to obtain an alkali metal iodide-impregnated material, drying the alkali metal iodide-impregnated material to obtain a dried material, and then heating (calcining) of the dried material (preferably in a non-oxidizing or reducing gas atmosphere such as hydrogen gas, or in an inert gas atmosphere such as nitrogen, helium and the like and combinations thereof) to obtain the final catalyst composition. Or, a supported palladium catalyst composition, preferably a $Pd/Al_2O_3$ composition (more preferably one which is commercially available, e.g., from Mallinckrodt Specialty Chemicals Company, Erie, Pa.), can be impregnated with an alkali metal iodide to obtain an alkali metal iodide-impregnated material, followed by drying the alkali metal iodide-impregnated material to obtain a dried material, and then heating the dried material (preferably in a non-oxidizing or reducing or inert gas atmosphere) to obtain the final catalyst composition. Or, the supported palladium catalyst composition can be impregnated with at least one alkali metal iodate to obtain an alkali metal iodate-impregnated material, followed by drying the alkali metal iodate-impregnated material to obtain a dried material, and then heating the dried material in a non-oxidizing or reducing gas atmosphere, preferably hydrogen gas (at a temperature sufficient to convert the alkali metal iodate to alkali metal iodide) to obtain the final catalyst composition.

The preferred starting material (also referred to as "base catalyst"), which is to be improved in accordance with this invention by incorporation of alkali metal iodide thereon or therein, can be any supported palladium-containing composition having the palladium concentrated in the skin of the composition. The base catalyst composition can be a fresh hydrogenation catalyst or it can be a used and thereafter regenerated hydrogenation catalyst composition. Broadly, the base catalyst can contain about 0.01 weight-% Pd (on a total catalyst composition weight basis) to about 2 weight-% Pd (preferably about 0.05 weight-% Pd to about 1 weight-% Pd), and a solid inorganic support material (listed above), preferably alumina (more preferably alpha-alumina). The supported Pd-containing base catalyst particles can have any suitable shape, and preferably are spherical pellets or cylindrical extrudates. The size of these supported base catalyst particles generally is in the range of from about 1 mm to about 10 mm, preferably in the range of from about 2 mm to about 6 mm, and its surface area generally is in the range of from about 1 $m^2/g$ to about 200 $m^2/g$.

In one preferred method of preparing the catalyst composition of this invention, a Pd-containing base catalyst (described above), which more preferably has been prereduced with hydrogen gas at room temperature (about 10° C. to about 40° C.), is contacted with a solution (preferably aqueous) of at least one alkali metal iodide (preferably KI) at such conditions as to obtain a final catalyst composition containing in the range of from about 0.02 weight-% of alkali metal (on a total catalyst composition weight basis) to about 10 weight-% of alkali metal (preferably in the range of from about 0.05 weight-% of alkali metal to about 5 weight-% of alkali metal) (preferably, the alkali metal is potassium). Generally, the concentration of the alkali metal iodide in the contacting (impregnating) solution (preferably aqueous) is in the range of from about 0.02 mol/l to about 10 mol/l (preferably in the range of from about 0.2 mol/l to about 3 mol/l). The preferred contacting method is "incipient wetness impregnation," i.e., essentially completely filling the pores of the base catalyst with the alkali metal iodide solution. Generally, the weight ratio of the solution to the solid base catalyst composition is in the range of from about 0.2:1 to about 2:1, preferably in the range of from about 0.4:1 to about 1:1 (depending on the alkali metal iodide concentration of the impregnating solution and the desired alkali metal iodide level to be attained in the catalyst composition of this invention). Thereafter, the impregnated catalyst composition is substantially dried (preferably at about 50° C. to about 150° C. for about 0.5 hour to about 20 hours) and heated in a non-oxidizing gas atmosphere (more preferably in a reducing gas such as $H_2$, or an inert gas such as $N_2$, He and the like and combinations thereof) at a temperature in the range of from about 300° C. to about 600° C. (preferably in the range of from about 300° C. to about 500° C.) for a time period in the range of from about 0.2 hour to about 20 hours (preferably in the range of from about 1 hour to about 10 hours).

In another preferred method of preparing the catalyst composition of this invention, a Pd-containing base catalyst (described above) is contacted with a solution (preferably aqueous) of at least one alkali metal iodate (preferably $KIO_3$) at such conditions to obtain a final catalyst composition containing in the range of from about 0.02 weight-% alkali metal (on a total catalyst composition weight basis) to about 10 weight-% alkali metal (preferably in the range of from about 0.05 weight-% alkali metal to about 5 weight-% alkali metal) (preferably, the alkali metal is potassium), wherein the concentration of the alkali metal iodate(s) in the impregnating solution is in the range of from about 0.02 mol/l to about 10 mol/l (preferably in the range of from about 0.2 mol/l to about 3 mol/l). The impregnating procedure is carried out essentially in accordance with the method described above for the impregnation with alkali metal iodide. Thereafter, the impregnated catalyst composition is substantially dried (as described above) and heated in a reducing gas (preferably $H_2$) at a temperature in the range of from about 200° C. to about 600° C. (preferably in the range of from about 300° C. to about 500° C.) for a time period in the range of from about 0.2 hour to about 20 hours (preferably in the range of from about 1 hour to about 10 hours) so as to convert said at least one alkali metal iodate to at least one alkali metal iodide.

In another preferred method of preparing the catalyst composition of this invention, the impregnated catalyst material is dried and heated (as described above) and then treated with one or more sulfur-containing compounds such as sulfides, disulfides, mercaptans, mercaptides, thiophenes, thiophanes, thiophenols, benzothiophenes, dibenzothiophenes and the like and combinations thereof. The presently preferred sulfur-containing compound is thiophene. The total amount of sulfur in the one or more sulfur-containing compounds is preferably about 100 parts-per-million (ppm) sulfur, more preferably about 75 ppm sulfur, and most preferably 50 ppm sulfur. Any suitable means known to one skilled in the art may be used to treat the dried and heated impregnated catalyst composition with the one or more sulfur-containing compounds. One preferred method is by soaking the dried and heated impregnated catalyst composition at about room temperature (approximately in the range of from about 20° C. to about 25° C.) for a time period in the range of from about 5 hours to about 20 hours (preferably in the range of from about 10 hours to about 18 hours) in a sulfur-compound-containing solution such as thiophene containing about 30 ppm sulfur.

The selective hydrogenation process of this invention can be carried out by contacting a fluid which comprises a highly unsaturated hydrocarbon, in the presence of hydrogen, with the catalyst composition disclosed above. Preferably the fluid containing a highly unsaturated hydrocarbon is or comprises an unsaturated alkene stream containing an alkyne, a diolefin, or both as an impurity, generally at a level in the range of from about 1 mg/Kg (ppm) to about 50,000 ppm of the fluid. The unsaturated alkene in the fluid can be ethylene, propylene, butenes, or combinations of two or more thereof. The highly unsaturated hydrocarbon can be, for example, an alkyne, a diolefin, or combinations of any two or more thereof. Examples of suitable alkynes include, but are not limited to, acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and mixtures of two or more thereof. The presently preferred alkyne is acetylene. These alkynes are primarily hydrogenated to the corresponding alkenes. For example, acetylene is primarily hydrogenated to ethylene, propyne is primarily hydrogenated to propylene, and the butynes are primarily hydrogenated to the corresponding butenes (1-butene, 2-butenes). Similarly, in the selective hydrogenation of diolefins, the diolefins are hydrogenated to the corresponding monoolefins such as, for example, 1,3-butadienes are selectively hydrogenated to butenes.

The catalyst composition of this invention can be employed directly in the selective hydrogenation process of the second embodiment of this invention. However, it is preferred to first treat the catalyst composition with a reducing gas such as hydrogen. Generally, the optimal operation of the selective hydrogenation does not begin until there has been a substantial reduction of the palladium component. Typically, the reduction can be carried out at a temperature in the range of from about 10° C. to about 200° C., preferably in the range of from about 20° C. to 100° C., for at least about 10 minutes, preferably in the range of from about 0.5 hour to about 10 hours, and most preferably in the range of from 1 hour to 10 hours.

Non-limiting examples of suitable diolefins, preferably containing 3 to 12 carbon atoms per molecule which can be hydrogenated in the process of this invention, include propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and mixtures of one or two of these diolefins. Presently preferred diolefins are propadiene, 1,3-butadiene, pentadienes (such as 1,3-pentadiene, 1,4-pentadiene, isoprene), cyclopentadienes (such as 1,3-cyclopentadiene) and dicyclopentadiene (also known as tricyclo[5.2.1]$^{2,6}$deca-3,8-diene). These diolefins are selectively hydrogenated to the monoolefins containing the same number of carbon atoms per molecule as the diolefins. For example, 1,3-butadiene is hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, 1,3-cyclopentadiene is hydrogenated to cyclopentene, and dicyclopentadiene is hydrogenated to dihydrocyclopentadienes (in particular, tricyclo[5.2.1]$^{2,6}$dec-3-ene).

The highly unsaturated hydrocarbon-containing fluid feed for the hydrogenation process of this invention can also comprise other hydrocarbons, in particular, monoolefins and aromatic hydrocarbons. Non-limiting examples of such other hydrocarbons which can be present in the feed at a level of at least 30 volume-% include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcylcooctenes, benzene, toluene, ethylbenzene, styrene, xylenes and the like, and mixtures of two or more than two of these hydrocarbons.

The fluid feed, which may be liquid or gaseous at the hydrogenating conditions of this process, generally comprises in the range of from about 0.1 weight-% of at least one diolefin to about 99.9 weight-% of at least one diolefin. The fluid feed can additionally comprise other hydrocarbons (at a level in the range of from about 0.1 weight-% to about 99.9 weight-%), in particular aromatic hydrocarbons, such as benzene, toluene, styrene and ethylbenzene, which may be present at a level in the range of from about 50 weight-% to about 99 weight-%. However, it is within the scope of this invention to employ feeds which contain about 100% of at least one diolefin, such as substantially pure dicyclopentadiene. Also, the feed can contain small amounts, generally less than about 0.05 weight %, in particular in the range of from about 10 ppm S to about 400 ppm S, of sulfur compounds (such as $H_2S$, carbonyl sulfide, carbon disulfide, mercaptans, organic sulfides such as thiophene, organic di-, tri- and tetrasulfides, and the like) as impurities. Carbon monoxide and/or water (generally less than about 0.05 mole-% of each) can also be present as impurities.

The selective hydrogenation process of this invention is generally carried out by contacting a feed stream containing at least one highly unsaturated hydrocarbon and molecular hydrogen with the catalyst of this invention which is generally contained in a fixed bed. Generally, in the range of from about 1 to about 10, preferably in the range of from about 1 to about 2, moles of hydrogen are employed for each mole of the highly unsaturated hydrocarbon present in the feed. The temperature necessary for the selective hydrogenation process of this invention depends largely upon the activity of the catalyst and the desired extent of diolefin hydrogenation. Generally, reaction temperatures in the range of from about 10° C. to about 300° C., preferably in the range of from about 20° C. to about 250° C., and most preferably 30° C. can be used. A suitable reaction pressure generally is in the range of from about 15 pounds per square inch gauge (psig) to about 2,000 pounds per square inch gauge (psig), preferably in the range of from about 50 psig to about 1,500 psig, and most preferably in the range of from 100 psig to 1,000 psig. The liquid hourly space velocity (LHSV) of the hydrocarbon feed can vary over a wide range. Typically, the space velocity of the feed will be in the range of from about 0.5 liter of hydrocarbon feed per liter of catalyst per hour (liter/liter/hour) to about 100 liters of hydrocarbon feed per liter of catalyst per hour, more preferably in the range of from about 2 liters/liter/hour to about 60 liters/liter/hour. The hydrogenation process conditions should be such as to avoid significant hydrogenation of monoolefins which are formed by hydrogenation of the highly unsaturated hydrocarbons being initially present in the feed to saturated hydrocarbons such as alkanes and cycloalkanes.

In a preferred embodiment, the at least one alkadiene is selected from the group consisting of propadiene, 1,3-butadiene, 1,3-pentadiene, 1,4-pentadiene and isoprene and is selectively hydrogenated with hydrogen gas to at least one alkene selected from the group consisting of butenes and pentenes in the presence of the catalyst composition of this invention. In another preferred embodiment, 1,3-cyclopentadiene is selectively hydrogenated with hydrogen gas to cyclopentene in the presence of the catalyst composition of this invention. In still another preferred embodiment, dicyclopentadiene is selectively hydrogenated with hydrogen gas to at least one dihydrodicyclopentadiene in the presence of the catalyst composition of this invention.

In one of the preferred embodiments of the diolefin hydrogenation process of this invention, a feed stream containing at least one pentadiene, such as, for example, 1,3-pentadiene and/or 1,4-pentadiene and/or isoprene and molecular hydrogen is contacted with the catalyst, generally contained in a fixed bed. Generally, the hydrocarbon feed contains other hydrocarbons, such as $C_4+$ alkanes (butanes, pentanes, hexanes), $C_4+$ alkenes (butenes, pentenes, hexenes) and aromatic hydrocarbons (benzene, toluene, ethylbenzene, styrene and the like). This preferred hydrogenation process generally employs in the range of from about 1 moles of $H_2$ per mole of pentadiene(s) to about 2 moles of $H_2$ per mole of pentadiene(s). The reaction temperature necessary for the selective hydrogenation of pentadiene depends largely upon the activity of the catalyst and the desired extent of the pentadiene hydrogenation, and generally is in the range of from about 35° C. to about 100° C. Generally, the total pressure is in the range of from about 50 pounds per square inch gauge (psig) to about 1,000 pounds per square inch gauge (psig). The liquid hourly space velocity (LHSV) of the hydrocarbon feed can also vary over a wide range. Typically, the liquid hourly space velocity will be in the range of from about 1 liter of hydrocarbon feed per liter of catalyst per hour (liters/liter/hour) to about 50 liters/liter/hour. The hydrogenation process conditions should be such as to avoid significant hydrogenation of pentenes to pentane.

In another preferred embodiment, dicyclopentadiene is selectively hydrogenated to dihydrodicyclopentadienes, mainly the dicyclopentene containing the double bond in the "3" position (i.e., tricyclo[5.2.1]$^{2,6}$dec-3-ene). In still another preferred embodiment, 1,3-butadiene is selectively hydrogenated to butenes. Operating conditions for these embodiments are substantially the same as those described above for the selective hydrogenation of pentadiene(s) to pentenes.

Also within the scope of this invention is to employ the catalyst composition in accordance with this invention for the selective hydrogenation of alkynes, preferably containing 2 to 12 carbon atoms, to the corresponding monoolefins (alkenes). The reaction conditions for the selective alkyne hydrogenation are approximately the same as those described above for the selective hydrogenation of diolefins to monoolefins.

If it is desired to regenerate the catalyst of this invention after prolonged use in a hydrogenation process, this can be accomplished by leaching the spent catalyst with water to dissolve the alkali metal iodide, calcining the leached catalyst in an oxidizing atmosphere (e.g., in air; at a temperature in the range of from about 500° C. to about 600° C.) to burn off carbonaceous deposits, reimpregnating the calcined catalyst with dissolved alkali metal iodide, and heating it (as is described for the fresh catalyst of this invention).

The following examples are presented to further illustrate this invention and should not be construed as unduly limiting the scope of this invention.

EXAMPLE I

This example illustrates the preparation of various palladium-containing skin catalysts and their use in the selective hydrogenation of 1,3-butadiene to butenes. The concentration of the palladium in a representative sample of the various palladium-containing skin catalysts, in the form of catalyst particles, was measured with an electron microprobe. A representative sample of the skin catalyst particles contained about 0.3 weight-% Pd (on a total catalyst composition weight basis) with an average of 51 weight-% of such palladium (on a palladium weight basis, thus the term "51 weight-% of such palladium" refers to 51 percent of the about 0.3 weight-% Pd) concentrated in an area within about 50 microns of the exterior surface of the catalyst particles, an average of 64 weight-% of such palladium (on a palladium weight basis) concentrated in an area within about 100 microns of the exterior surface of the catalyst particles, and an average of 72 weight-% of such palladium (on a palladium weight basis) concentrated in an area within about 150 microns of the exterior surface of the catalyst particles. An average of 88 weight-% of such palladium (on a palladium weight basis) was concentrated in an area within about 300 microns of the exterior surface of the catalyst particles.

See Example VII for a description of the measurement of the skin thickness of palladium (i.e., depth of palladium deposition) on a support surface as well as representative data used to obtain the above-described average weight percents of palladium within certain microns of the exterior surface of the 0.3 weight-% Pd catalyst particles.

Catalyst A (Control) was a Pd/Al$_2$O$_3$ skin catalyst of spherical shape, which had been provided by the Calsicat Catalyst Division of Mallinckrodt Specialty Chemicals Company, Erie, Pa. under the product designation "E-143 SDU". This catalyst had a BET/N$_2$ surface area of 35 m$^2$/g, and a particle size of $\frac{1}{16}$ inch (approximately 1.6 mm). Catalyst A contained 0.3 weight-% Pd.

Catalyst B (Control) was a Pd/Ag/KF/Al$_2$O$_3$ catalyst. It was prepared as follows: 80.23 grams of Catalyst A were soaked in an aqueous solution of 4.05 grams of AgNO$_3$ in 72.7 grams of distilled H$_2$O for about 1.5 hours. Excess liquid was drained from the Ag-impregnated catalyst, which was then dried at 180° F. overnight and calcined for 3 hours at 370° C. in air. A sample of 20.18 grams of this calcined Pd/Ag/Al$_2$O$_3$ catalyst (labeled "Catalyst X") was then soaked with a solution of 0.47 g potassium fluoride in 14.1 cc of H$_2$O, while occasionally stirring the mixture. The thus-obtained KF-impregnated Pd/Ag/Al$_2$O$_3$ catalyst was dried for several hours at 180° F. and calcined in air at 370° C. for 4 hours. Catalyst B contained about 0.28 weight-% Pd, about 1.6 weight-% Ag, and about 1.5 weight-% K (as KF).

Catalyst C (Control) was a Pd/Ag/KI/Al$_2$O$_3$ catalyst. It was prepared by prereducing 20.15 grams of Catalyst X (described above) for about 1 hour with H$_2$ gas at room temperature. Thereafter, the H$_2$-treated catalyst material was soaked at room temperature with a solution of 0.89 g potassium iodide in about 12.0 g distilled water. The KI-impregnated catalyst material was dried at room temperature and heated for 5 hours in nitrogen gas at 400° C. Catalyst C contained about 0.28 weight-% Pd, about 2.6 weight-% Ag and about 1.0 weight-% K (as KI).

Catalyst D (Invention) was a Pd/KI/$Al_2O_3$ catalyst. It was prepared by prereducing 20.6 grams of Catalyst A for about 0.5 hours in a hydrogen gas stream at room temperature, and then soaking the prereduced material with a solution of 0.87 gram potassium iodide in 12.8 grams of water. The KI-impregnated catalyst material was dried over night at room temperature and then heated for about 24 hours in nitrogen gas at 400° C. Catalyst D contained about 0.3 weight-% Pd and about 1.0 weight-% K (as KI). It contained no Ag.

EXAMPLE II

Catalysts A–D (described above) were tested in the selective hydrogenation of 1,3-butadiene by the following procedure. About 20 cc of each catalyst was placed into a stainless steel reactor tube having an inner diameter of 0.5 inch and a length of about 18 inches. Thermocouples were inserted into the top and bottom regions of the catalyst bed, which was heated by an external furnace. The hydrocarbon feed was liquid and contained about 79 weight-% 1,3-butadiene, about 13 weight-% of various butenes, about 6 weight-% butanes (mainly n-butane), about 0.3 weight-% 1,2-butadiene, about 0.2 weight-% 1-butyne and about 1.5 weight-% vinyl acetylene. The liquid feed rate was about 1 cc/minute in all tests. Hydrogen gas was fed with the liquid hydrocarbon feed so as to provide a $H_2$/butadiene mole ratio of about 1:1. The total pressure in the reactor was maintained at about 500 psig, and the average reaction temperature was in the range of from about 100° F. to about 120° F. Generally, a portion of the reaction product was recycled to the inlet of the reactor so as to provide a volume ratio of recycle stream to fresh feed stream of about 33:1. The non-recycled product gas was analyzed at various time intervals (generally at intervals of about 1 hour to about 3 hours) by means of a gas chromatograph. Pertinent test results (obtained after a steady state of the reaction was attained) are summarized in Table I.

Test data in Table I show that Invention Catalyst D consistently performed better than control Catalysts A–C, as evidenced by lower yields of "heavies" ($C_6$+ hydrocarbons, i.e., hydrocarbons containing at least 6 carbon atoms per molecule), which tend to accumulate on the catalyst surface and contribute to the gradual deactivation of the catalyst. Test data in Table I also show that control Catalyst C (a Pd/KI/$Al_2O_3$ catalyst which contained silver) selectively hydrogenated approximately 18.4 weight percent (on a total feed weight basis) 1,3-butadienes. Invention Catalyst D (a Pd/KI/$Al_2O_3$ catalyst which did not contain silver) selectively hydrogenated approximately 73.8 weight percent (on a total feed weight basis) 1,3-butadienes. Thus, control Catalyst C, which contained silver, selectively hydrogenated approximately 55 weight percent (on a total feed weight basis) fewer highly unsaturated hydrocarbons (1,3-butadienes) to less unsaturated hydrocarbons (such as, 1-butenes) than Invention Catalyst D which did not contain silver.

EXAMPLE III

This example illustrates the selective hydrogenation of dicyclopentadiene to dihydrodicyclopentadiene in the presence of various alumina-supported palladium catalysts (described in Example I).

Hydrogenation tests were carried out as follows. A stainless steel reactor tube (total length: about 18 inches; inner diameter: 0.5 inch) was filled with a bottom layer of about 20–30 cc of "36-grit" Alundum® (alumina having a surface area of less than 1 $cm^2$/g), a middle layer of about 20 cc of a particular Pd-containing catalyst, and a top layer of about 20–30 cc of "36-grit" Alundum®. Glass wool was placed below each of the two Alundum® layers and the catalyst layer. Each employed catalyst was activated by passing hydrogen gas (flow rate: 100 cc $H_2$ per minute) for 2 hours through the reactor at a temperature of 100° F. Thereafter, a solution of 10 weight-% dicyclopentadiene (DCP) in cyclohexane was introduced (in a downflow mode) into the reactor at a rate of about 1 cc per minute, together with hydrogen gas as cofeed. The $H_2$ flow rate generally ranged from about 10 cc/minute to about 50 cc/minute, and the reaction temperature generally ranged from about 100° F. to about 150° F. No product recycle was carried out. The liquid product effluent (i.e., the cyclohexane-diluted product) was analyzed by means of a gas chromatograph at various time intervals (generally at 0.5 hour to 1 hour intervals). Pertinent test data are summarized in Table II.

TABLE I

| Catalyst | 1,3-Butadiene | 1-Butene | Cis-2-Butene | Trans-2-Butene | n-Butane | $C_6$ + Hydrocarbons |
|---|---|---|---|---|---|---|
| Feed | Average Weight Percentage of Compounds in Feed | | | | | |
| Feed I (for Runs 1–4) | 78.8 | 7.6 | 2.2 | 2.8 | 6.2 | 0.06 |
| Feed II (for Runs 5–6) | 79.1 | 7.4 | 2.2 | 2.7 | 6.1 | 0.14 |
| Test Run | Average Weight Percentage of Compounds in Product | | | | | |
| Run 1 (Control) A (Pd/$Al_2O_3$) | 7.0 | 53.2 | 5.4 | 27.2 | 6.8 | 0.32 |
| Run 2 (Control) B (Pd/Ag/KF/$Al_2O_3$) | 7.5 | 51.7 | 6.6 | 25.4 | 8.4 | 0.30 |
| Run 3* (Control) C (Pd/Ag/KI/$Al_2O_3$) | 60.4 | 19.8 | 3.3 | 9.4 | 6.4 | 0.28 |
| Run 4 (Invention) D (Pd/KI/$Al_2O_3$) | 5.0 | 50.9 | 6.5 | 29.3 | 7.9 | 0.17 |
| Run 5 (Control) A (Pd/$Al_2O_3$) | 3.3 | 52.4 | 6.9 | 28.6 | 8.1 | 0.40 |
| Run 6 (Invention) D (Pd/KI/$Al_2O_3$) | 3.9 | 50.9 | 6.6 | 30.5 | 7.6 | 0.20 |

*No product recycle was carried out

TABLE II

| | | | | Average Content (Wt-%) of Compound in Reactor Effluent | | |
|---|---|---|---|---|---|---|
| Run | Catalyst | Reaction Temp. (° C.) | $H_2$ Flow Rate (cc/min) | Dicyclopentadiene | Dihydro-dicyclopentadiene | Tetrahydro-dicyclopentadiene |
| 7 (Control) | A ($Pd/Al_2O_3$) | 133 | 45 | 0.05 | 0.2 | 9.0 |
| | | 143 | 45 | 0.15 | 0.5 | 9.4 |
| 8 (Control) | B ($Pd/Ag/KF/Al_2O_3$) | 114 | 30 | 0.06 | 2.2 | 6.2 |
| 9 (Invention) | D ($Pd/KI/Al_2O_3$) | 107 | 30 | 1.9 | 4.0 | 3.4 |
| | | 107 | 45 | 1.9 | 4.1 | 3.1 |
| | | 132 | 45 | 0.9 | 4.3 | 3.3 |
| | | 142 | 45 | 0.8 | 4.4 | 3.3 |
| 10 (Control) | A* ($Pd/Al_2O_3$) | 107 | 25 | 0.03 | 0.3 | 7.3 |
| 11 (Invention) | D* ($Pd/KI/Al_2O_3$) | 103 | 30 | 0.9 | 8.6 | 0.3 |
| | | 125 | 45 | 1.0 | 8.3 | 0.3 |
| | | 145 | 50 | 0.2 | 8.3 | 0.5 |

*Catalyst was soaked for about 16 hours at room temperature in gasoline containing about 30 ppm sulfur (mainly thiophene), and was dried before the test.

Test data in Table II show that in Run 9 which employed invention Catalyst D, the yield of the desired dihydrodicyclopentadiene was much higher than in Runs 7 and 8 employing control Catalysts A and B. When invention Catalyst D had been treated with sulfur compounds, before it was used for the hydrogenation of dicyclopentadiene, the selectivity to dihydrodicyclopentadiene was even higher than that achieved with untreated Catalyst D (Run 11 vs. Run 9), whereas the sulfur-treated Catalyst A was still far inferior in terms of selectivity to dihydrodicyclopentadiene (Run 10).

EXAMPLE IV

In this example, the production of additional $Pd/Al_2O_3$-containing skin catalysts is described. The concentration of the palladium in a representative sample of the additional $Pd/Al_2O_3$-containing skin catalysts, in the form of catalyst particles, was measured with an electron microprobe. The representative sample of the skin catalyst particles contained about 0.5 weight-% Pd (on a total catalyst composition weight basis) with an average of 73 weight-% of such palladium (on a palladium weight basis, thus the term "73 weight-% of such palladium" refers to 73 percent of the about 0.5 weight-% Pd) concentrated in an area within about 50 microns of the exterior surface of the catalyst particles, an average of 89 weight-% of such palladium (on a palladium weight basis) concentrated in an area within about 100 microns of the exterior surface of the catalyst particles, and an average of 92 weight-% of such palladium (on a palladium weight basis) concentrated in an area within about 150 microns of the exterior surface of the catalyst particles. An average of 97 weight-% of such palladium was concentrated in an area within about 300 microns of the exterior surface of the catalyst particles.

See Example VII for a description of the measurement of the skin thickness of palladium (i.e., depth of palladium deposition) on a support surface as well as representative data used to obtain the above-described average weight percents of palladium within certain microns of the exterior surface of the 0.5 weight-% Pd catalyst particles.

Catalyst A1 (Control) was essentially the same as Catalyst A ($Pd/Al_2O_3$, described in Example I) except that Catalyst A1 contained about 0.5 weight-% Pd (in lieu of 0.3 weight-% Pd). It was supplied by the Calsicat Catalyst Division of Mallinckrodt, Specialty Chemicals Company, Erie, Pa., under the product designation "E-144 SDU".

Catalyst B1 (Control) was essentially the same as Catalyst B ($Pd/Ag/KF/Al_2O_3$, described in Example I) except that it contained about 0.5 weight-% Pd (in lieu of about 0.3 weight-% Pd). It was prepared substantially in accordance with the method described for Catalyst B, except that Catalyst A1 was used as the starting material (in lieu of Catalyst A). Catalyst B1 contained about 0.5 weight-% Pd, about 2.6 weight-% Ag and about 2.6 weight-% K.

Catalyst B2 (Control) was a $Pd/KF/Al_2O_3$ catalyst containing about 0.5 weight-% Pd and about 2.5 weight-% K. It was essentially the same as Catalyst B1, except that no silver was present. It was prepared by impregnating 20.6 grams of Catalyst A1 ($Pd/Al_2O_3$; described above) with a solution of 0.75 grams of potassium fluoride in 12.0 grams of water, followed by drying overnight at 71° C. (160° F.) and calcining for 2 hours at 380° C.

Catalyst C1 (Control) was essentially the same as Catalyst C ($Pd/Ag/KI/Al_2O_3$ described in Example I) except that Catalyst C1 contained about 0.5 weight-% Pd (in lieu of 0.3 weight-% Pd). It was prepared essentially in accordance with the preparation method for Catalyst C except that Catalyst A1 (in lieu of Catalyst A) was used for preparing the starting material (labeled "Catalyst X1"), which was then used to make Catalyst C1. Catalyst C1 contained about 0.5 weight-% Pd, about 2.6 weight-% Ag and about 1.6 weight-% K.

Catalyst D1 (Invention) was a $Pd/KI/Al_2O_3$ catalyst (similar to Catalyst D, described in Example I). Catalyst D1 was prepared by prereducing 40.3 g of Catalyst A1 for about 40 minutes in a hydrogen stream at room temperature, impregnating the prereduced material with a solution of 1.50 g of potassium iodide in 24.0 g distilled $H_2O$, drying the KI-impregnated material at room temperature, and heating it in a nitrogen stream at 380°0 C. for about 4 hours. Catalyst D1 contained about 0.5 weight-% Pd, about 0.7 weight-% K and about 2.1 weight-% I. It contained no Ag.

Catalyst D2 (Invention) was essentially the same as Catalyst D1, except that 0.67 g KI was used (in lieu of 1.50 g KI) and the final heating of the $Pd/KI/Al_2O_3$ material was carried out for 3 hours in hydrogen gas at 400° C. (rather than in $N_2$ at 380° C.).

Catalyst D3 (Invention was a $Pd/KI/Al_2O_3$ which was prepared using $KIO_3$ instead of KI. A sample of 40.3 grams of Catalyst A1 was soaked for about 45 minutes with a solution of 0.45 g potassium iodate in 21.7 g water. The $KIO_3$-impregnated $Pd/Al_2O_3$ material was dried for several days at 180° F. and was then treated for 4 hours in a hydrogen gas stream at 404° C. (so as to substantially reduce $KIO_3$ to $KI$). Catalyst D3 contained about 0.5 weight-% Pd and about 0.2 weight-% K. It contained no Ag.

about 500 psig, and the $H_2$ flow rate was about 25 cc/minute to about 125 cc/minute. The cooled liquid reactor effluent was analyzed by means of a gas chromatograph. Pertinent test data are summarized in Table IV.

TABLE IV

| | | | Average Weight Percentage of component in Feed Product[1] | | | | | | |
|---|---|---|---|---|---|---|---|---|---|
| Run | Catalyst | Feed | Aliphatic Pentadienes | Aliphatic Pentenes | 1,3-Cyclo-pentadiene | Cyclo-pentene | Dicyclo-pentadiene | Dihydrodicyclo-pentadiene | Tetrahydro-dicyclopentadiene |
| 12 (Control) | A1 (Pd/$Al_2O_3$) | III | ~0 | 2.0 | 0.1 | 0.4 | 1.2 | 4.2 | 2.5 |
| 13 (Control) | C1 (Pd/Ag/KI/$Al_2O_3$) | III | —[2] | —[2] | —[2] | —[2] | —[2] | —[2] | —[2] |
| 14 (Invention) | D1 (Pd/KI/$Al_2O_3$) | III | <0.1 | 2.5 | <0.1 | 0.9 | 0.2 | 8.0 | 0.4 |
| 15 (Control) | B1 (Pd/Ag/KF/$Al_2O_3$) | IV | 0.1 | 4.0 | 0.2 | 1.0 | 2.1 | 6.0 | 1.4 |
| 16 (Control) | B2 (Pd/KF/$Al_2O_3$) | IV | 0.1 | 3.7 | 0.1 | 0.8 | 1.8 | 5.8 | 2.2 |
| 17 (Invention) | D1 (Pd/KI/$Al_2O_3$) | IV | 0.1 | 4.7 | <0.1 | 1.7 | 0.6 | 8.5 | 0.4 |

[1]Product formed at reaction conditions selected to achieve ~80% conversion of styrene (to ethylbenzene).
[2]Catalyst was not active enough to achieve 80% conversion of styrene.

EXAMPLE V

This example illustrates the selective hydrogenation of $C_5$+ diolefins (contained as minor components in aromatic-rich pyrolysis gasoline) employing catalysts described in Example IV.

The feeds employed in the following hydrogenation tests were refinery streams (from an ethane pyrolysis reactor) called "debutanized aromatic concentrate" (DAC). Approximate compositions of three feeds are listed in Table III.

TABLE III

| | Weight Percentage of Compounds | | |
|---|---|---|---|
| Compound | Feed III | Feed IV | Feed V |
| 1-Pentene | 0.9 | 1.2 | 2.6 |
| 2-Pentene | 0.2 | 0.3 | 0.7 |
| Isoprene | 0.9 | 2.0 | 3.7 |
| 1,3-Pentadiene | 0.9 | 1.5 | 3.1 |
| 1,4-Pentadiene | 0.3 | 0.6 | 1.1 |
| 1,3-Cyclopentadiene | 1.4 | 2.1 | 2.7 |
| Cyclopentene | 0.9 | 1.4 | 2.8 |
| Benzene | 73.3 | 67.7 | 54.0 |
| Toluene | 4.4 | 1.4 | 11.2 |
| Ethylbenzene | 0.3 | <0.1 | 0.7 |
| Styrene | 1.7 | 2.1 | 3.0 |
| Dicyclopentadiene | 7.6 | 9.0 | 0.2 |
| Heavies | 1.3 | 1.7 | 0.2 |
| Sulfur | —* | ~0.001 | 0.01 |

Note:
Feed V was a light (overhead) DAC fraction from which dicyclopentadiene and heavies had been substantially removed (by fractional distillation).
*Not determined (estimated to be 0.002–0.005 weight % S).

The above-described feed was hydrogenated substantially in accordance with the procedure described in Example II, except that no product recycle was carried out. The temperature and the hydrogen flow were adjusted to hydrogenate about 80% of styrene contained in the feed (mainly to ethylbenzene), so as to operate tests employing different catalysts at conditions of comparable hydrogenation severity. Generally, the reaction temperature was about 120° F. to about 250° F., the reaction pressure was about 350 psig to Test data in Table IV clearly show that Runs 14 and 17 employing invention Catalyst D1 (Pd/KI/$Al_2O_3$) produced the desired monoolefins (aliphatic pentenes, cyclopentene and dihydrodicyclopentadiene) at higher yields than runs employing control catalysts. Thus, the invention catalyst exhibited higher selectivity to monoolefins than various Pd-containing control catalysts.

Results of three additional test runs (not included in Table IV) employing Feed V and operating at such conditions as to achieve a styrene conversion of 90% to 95% indicated that invention Catalysts D2 and D3 (described in Example IV) achieved almost complete conversions of aliphatic pentadienes to pentenes and of cyclopentadienes to cyclopentene, whereas control Catalyst A1 was considerably less selective to the $C_5$ monoolefins.

Figure 1:
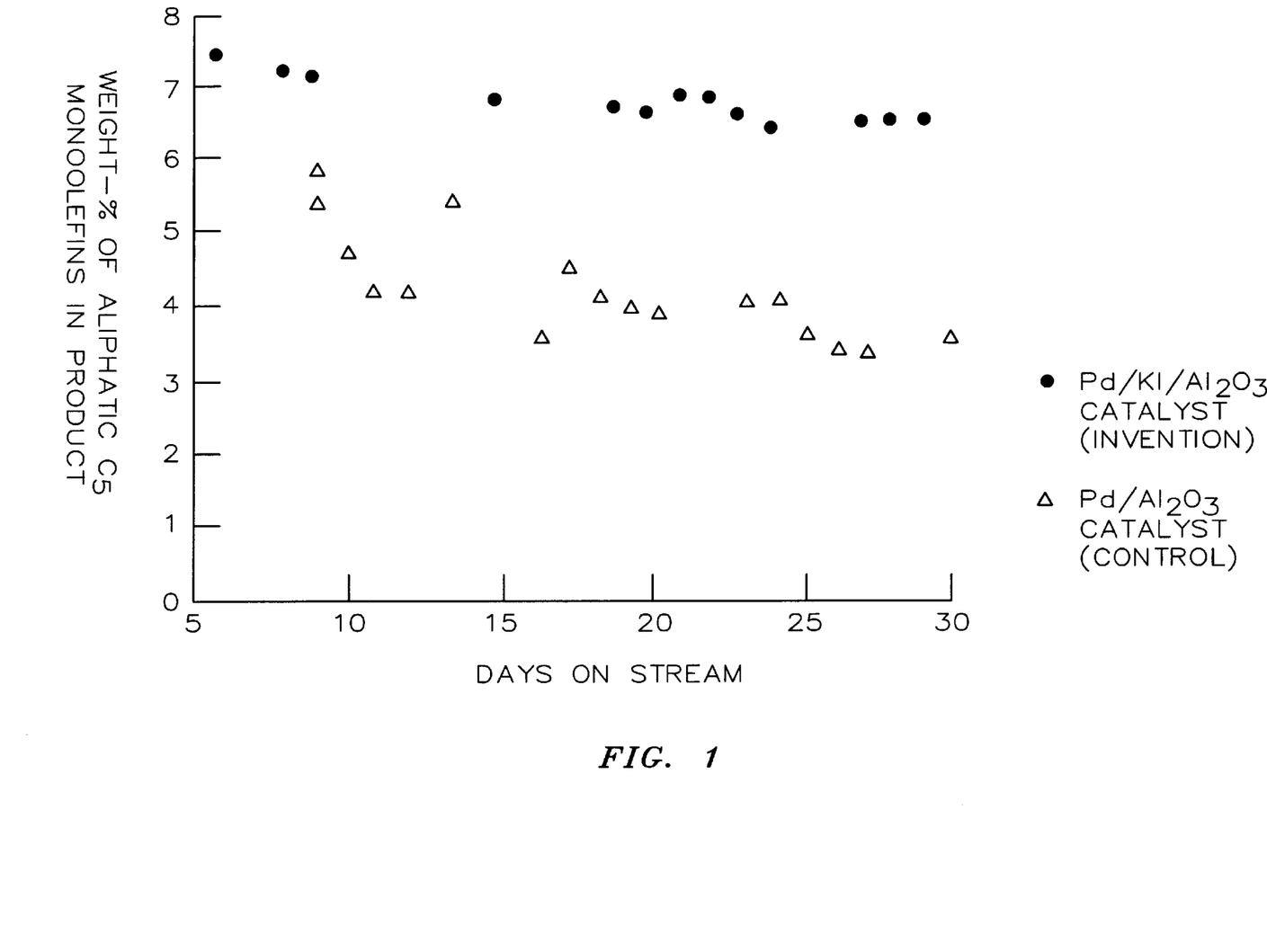
FIG. 1 illustrates the advantages of an invention catalyst over a control catalyst in the selective hydrogenation of diolefins to monoolefins.

Results of two month-long comparative tests for hydrogenating a prefractionated debutanized aromatic concentrate (DAC), which was similar to Feed V, employing an invention catalyst and a control catalyst are shown in FIG. 1. In both tests, the feed contained about 2.3 weight-% aliphatic $C_5$ monoolefins to about 2.5 weight-% aliphatic $C_5$ monoolefins and about 5.7 weight-% aliphatic $C_5$ diolefins to about 5.9 weight-% aliphatic $C_5$ diolefins. The graphs in FIG. 1 demonstrate that the invention catalyst (Pd/KI/$Al_2O_3$, essentially the same as Catalyst D2) was considerably more selective to $C_5$ monoolefins than a corresponding control catalyst (Pd/$Al_2O_3$, essentially the same as Catalyst A1), and exhibited excellent stability over a time period spanning from the fifth day to the thirtieth day of the hydrogenation reaction. Both tests were run at such conditions as to attain approximately the same styrene conversion (about 92% to about 95%). At these conditions, essentially complete conversion of all aliphatic $C_5$ diolefin was achieved. The most pertinent reaction conditions of the run employing the invention catalyst (Pd/KI/$Al_2O_3$) were: reaction temperature of about 170° F. to about 210° F., reaction pressure of about 340 psig to about 360 psig, DAC feed rate of about 0.9 cc/minute to about 1.1 cc/minute, and $H_2$ feed rate of about 65 cc/minute to about 75 cc/minute. A portion of the reaction product was recycled to the inlet of the reactor so as to provide a volume ratio of recycle stream to fresh feed stream of about 1:1.

EXAMPLE VI

This example illustrates the selective hydrogenation of an alkyne (methylacetylene, MA), in conjunction with diolefins (in particular propadiene, PD) contained in a propane feed (from a commercial ethylene plant).

The following catalysts were employed in comparative hydrogenation runs: Catalyst A ($Pd/Al_2O_3$; containing about 0.3 weight-% Pd; see Example I); Catalyst B3 ($PdAg/KF/Al_2O_3$) which was prepared substantially in accordance with the method for preparing Catalyst B and contained about 0.3 weight-% Pd, about 1.4 weight-% Ag, and about 1.3 weight-% K as KF; see Example I); and Catalyst D4 ($Pd/KI/Al_2O_3$) which was prepared substantially in accordance with the procedure for Catalyst D3 (described in Example IV), except that Catalyst D4 contained 0.3 weight-% Pd and 0.48 weight-% K (as KI).

The hydrogenation tests were carried out substantially in accordance with the procedure described in Example II, except that a liquefied propane feed was used. This propane feed contained 94.65 weight-% propane, 1.10 weight-% propylene, 1.08 weight-% propadiene (PD), 2.60 weight-% methylacetylene (MA, propyne), 0.07 weight-% 1-butene, 0.21 weight-% butadienes, and traces of $C_6$+ hydrocarbons. The feed rate of fresh liquid propane was about 1.4 cc/minute, the $H_2$ feed rate was in the range of from about 15 cc/minute to about 30 cc/minute, the reaction pressure was about 320 psig, and the reaction temperature was in the range of from about 80° F. to about 100° F. A major portion of the product was recycled to the reactor. The rate of recycled product to fresh propane feed was about 6:1. Product samples were analyzed by means of a gas chromatograph. Pertinent test results are summarized in Table V.

TABLE V

| Catalyst | $H_2$ Flow Rate (cc/minute) | Content of Component in Product (Weight %) | | | | | | % Conversion | | |
|---|---|---|---|---|---|---|---|---|---|---|
| | | Propylene | PD[1] | MA[2] | Butenes | Butadiene | $C_6^{+3}$ | MA[2] | PD[1] | (MA + PD) |
| A (Control) | 15 | 2.98 | 0.63 | 0.73 | 0.11 | 0.18 | 0.28 | 71.6 | 42.1 | 63.0 |
| B3 (Control) | 15 | 3.48 | 0.43 | 0.55 | 0.18 | 0.10 | 0.25 | 78.8 | 60.1 | 73.3 |
| D4 (Invention) | 15 | 3.25 | 0.67 | 0.59 | 0.11 | 0.17 | 0.06 | 77.3 | 38.3 | 65.8 |
| A (Control) | 20 | 3.90 | 0.18 | 0.25 | 0.22 | 0.06 | 0.42 | 90.6 | 83.1 | 88.4 |
| B3 (Control) | 20 | 4.13 | 0.16 | 0.17 | 0.25 | 0.04 | 0.29 | 93.5 | 85.4 | 91.1 |
| D4 (Invention) | 20 | 4.14 | 0.38 | 0.17 | 0.18 | 0.11 | 0.07 | 93.3 | 65.0 | 85.0 |
| A (Control) | 25 | 3.19 | 0.08 | 0.10 | 0.23 | 0.03 | 0.39 | 96.1 | 92.4 | 95.0 |
| B3 (Control) | 25 | 3.93 | 0.04 | 0.13 | 0.25 | 0.01 | 0.21 | 99.5 | 96.0 | 98.5 |
| D4 (Invention) | | 4.35 | 0.07 | 0.00 | 0.26 | 0.02 | 0.05 | 100.0 | 93.8 | 98.2 |
| A (Control) | 30 | 2.84 | 0.05 | 0.02 | 0.24 | 0.02 | 0.35 | 99.2 | 95.3 | 98.1 |
| B3 (Control) | 30 | 3.55 | 0.01 | 0.00 | 0.24 | 0 | 0.14 | 100.0 | 99.2 | 99.8 |
| D4 (Invention) | 30 | 3.61 | 0.01 | 0.00 | 0.26 | 0 | 0.05 | 100.0 | 99.0 | 99.7 |

[1]propadiene
[2]methylacetylene
[3]hydrocarbons containing 6 or more than 6 carbon atoms per molecule.
Note: The propane content in the product was about the same in all runs (about 95–96 weight %).

Figure 2:
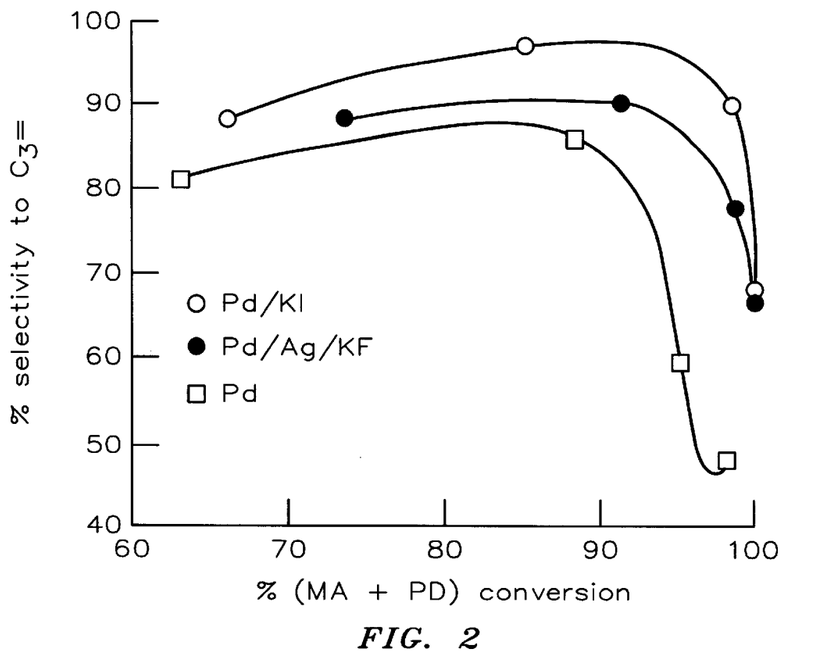
FIG. 2 shows the selectivity to propylene in a selective hydrogenation of acetylene at different conversions of methylacetylene and propadiene.
Figure 3:
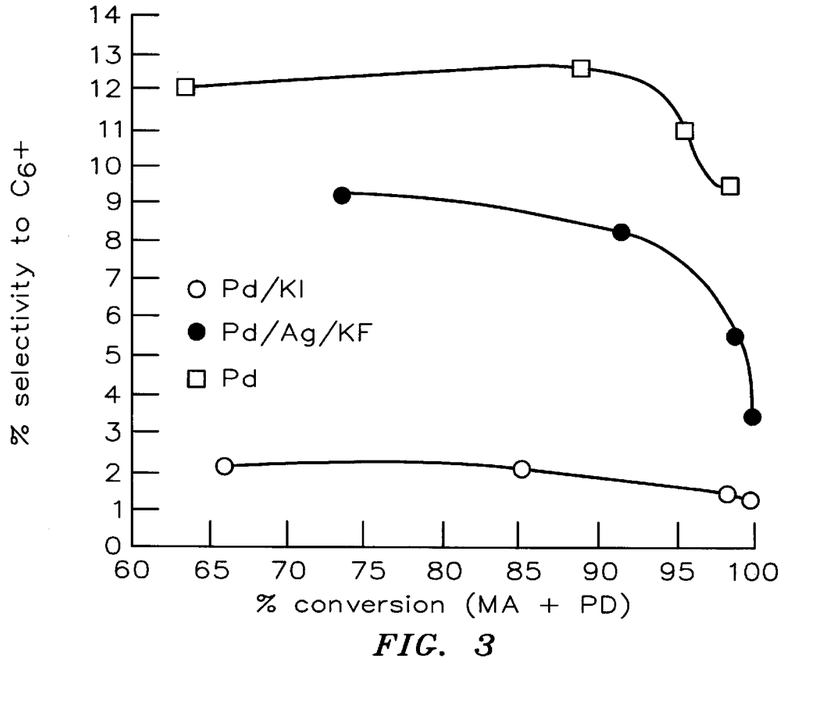
FIG. 3 shows the selectivity to $C_6+$ hydrocarbons in a selective hydrogenation of acetylene at different conversions of methylacetylene and propadiene.

Test data in Table V show that the $Pd/KI/Al_2O_3$ catalyst of this invention (Catalyst D4) consistently produced less undesirable heavies ($C_6$+ hydrocarbons) than the two control catalysts, at comparable conversions of (MA+PD). Selectivities to desirable propylene and to undesirable $C_6$+ hydrocarbons, respectively, at various (MA+PD) conversions are presented in FIG. 2 and FIG. 3, respectively. The selectivities were calculated by dividing the yield of a product component by the combined conversion of MA (methylacetylene) and PD (propadiene). These figures indicate that the catalyst of this invention ($Pd/KI/Al_2O_3$) consistently converted methylacetylene and propadiene at a higher selectivity to propylene (a desired product) and at a lower selectivity to undesirable $C_6$+ hydrocarbons than the two control catalysts, at equal (MA+PD) conversions.

EXAMPLE VII

This example illustrates the measurement of the skin thickness of palladium (i.e., depth of palladium deposition) on a support surface as well as representative data used to obtain the above-described average weight percents of palladium within certain microns of the exterior surface of the 0.3 weight-% Pd catalyst particles (EXAMPLE I) and 0.5 weight-% Pd catalyst particles (EXAMPLE IV).

The runs were carried out as follows. SAMPLE I contained representative 0.3 weight-% Pd (on a total catalyst composition weight basis) catalyst particles consisting of 13 Control Catalyst A particles (See EXAMPLE I). SAMPLE II contained representative 0.5 weight-% Pd (on a total catalyst composition weight basis) catalyst particles consisting of 10 Control Catalyst A1 particles (See EXAMPLE IV).

For each sample, the catalyst particles were embedded in epoxy (obtained from Buehler, Ltd., Lake Bluff, Ill.) and allowed to polymerize overnight. A thin cut was made with a Buehler Isomet diamond saw to expose the interior of the embedded particles. This exposed surface was polished through successively smaller grit polishing media, finishing with submicron colloidal silica. Each polished sample was coated with a thin layer of carbon in a vacuum evaporator to provide conductivity for examination in the electron microprobe.

The instrument used for the analyses was a JEOL 733 electron microprobe with Noran Voyager stage and spectrometer automation. Instrument parameters included: 20 kilovolts accelerating voltage, 40 nanoamp beam current, and a focused electron beam. Line traverses to determine the metal deposition in the particle interior were set up to start at the outer rim of the particle (i.e., exterior surface of the particle) and to end at or near the center of the particle. Intervals between the analysis points were varied to define the deposition profile. Within the outer 300 micrometers of the traverse, the interval ranged from 2 micrometers to 10 micrometers.

The following Table VI illustrates the representative data used to obtain the above-described average weight percents of palladium within certain microns of the exterior surface of the 0.3 weight-% Pd catalyst particles (SAMPLE I). The following Table VII illustrates the representative data used to obtain the abovedescribed average weight percents of palladium within certain microns of the exterior surface of the 0.5 weight-% Pd catalyst particles (SAMPLE II).

TABLE VI

Sample I[1]

Average Weight Percentage of Palladium in the Catalyst Particle[2]

| Distance from Exterior Surface of Catalyst Particle | 1 | 2 | 3 | 4 | 5 | 6 | 7 | 8 | 9 | 10 | 11 | 12 | 13 | Total Avg. Weight Percentage of Palladium in the 13 Particles[2] |
|---|---|---|---|---|---|---|---|---|---|---|---|---|---|---|
| 0–50 um[3] | 48.5 | 27.8 | 57.5 | 36.3 | 82.4 | 54.5 | 36.6 | 54.8 | 77.6 | 43.3 | 70.2 | 40.7 | 36.9 | 51.3 |
| 50–100 um | 11.1 | 12.4 | 11.1 | 14.4 | 8.9 | 10.2 | 18.8 | 11.6 | 6.5 | 17.6 | 13.0 | 11.9 | 14.3 | 12.4 |
| 100–150 um | 10.1 | 9.7 | 8.3 | 12.1 | 2.9 | 7.9 | 9.3 | 7.7 | 4.3 | 12.6 | 6.1 | 13.4 | 10.0 | 8.8 |
| 150–200 um | 8.8 | 8.9 | 9.0 | 7.7 | 1.0 | 5.4 | 5.3 | 6.7 | 3.4 | 5.2 | 3.2 | 12.6 | 9.3 | 6.7 |
| 200–250 um | 5.3 | 10.4 | 4.5 | 6.4 | 1.0 | 4.1 | 5.4 | 6.2 | 2.2 | 4.1 | 2.1 | 5.2 | 7.3 | 4.9 |
| 250–300 um | 3.4 | 6.8 | 2.4 | 5.8 | 1.1 | 4.5 | 5.7 | 3.4 | 1.3 | 3.9 | 1.6 | 3.8 | 5.5 | 3.8 |
| >300 um | 12.8 | 24.0 | 7.2 | 17.3 | 2.7 | 13.4 | 18.9 | 9.6 | 4.7 | 13.3 | 3.8 | 12.4 | 16.7 | 12.1 |
| SUM | 100.0 | 100.0 | 100.0 | 100.0 | 100.0 | 100.0 | 100.0 | 100.0 | 100.0 | 100.0 | 100.0 | 100.0 | 100.0 | 100.0 |

[1]Catalyst particles containing 0.3 weight-% palladium (on a total catalyst composition weight basis).
[2]On a palladium weight basis (i.e., values given are percentages of the 0.3 weight-% palladium).
[3]0 μm indicates the exterior surface of the catalyst particle.

TABLE VII

Sample II[1]

Average Weight Percentage of Palladium in the Catalyst Particle[2]

| Distance from Exterior Surface of Catalyst Particle | 1 | 2 | 3 | 4 | 5 | 6 | 7 | 8 | 9 | 10 | Total Avg. Weight Percentage of Palladium in the 10 Particles[2] |
|---|---|---|---|---|---|---|---|---|---|---|---|
| 0–50 um[3] | 40.78 | 69.59 | 73.65 | 77.46 | 78.58 | 82.19 | 89.43 | 73.68 | 81.24 | 59.30 | 72.59 |
| 50–100 um | 27.56 | 12.72 | 16.35 | 14.27 | 14.12 | 7.82 | 3.86 | 19.42 | 14.44 | 29.21 | 15.98 |
| 100–150 um | 5.36 | 9.21 | 2.83 | 1.91 | 3.40 | 2.26 | 1.64 | 4.61 | 1.01 | 4.40 | 3.66 |
| 150–200 um | 7.62 | 4.11 | 1.73 | 1.22 | 0.85 | 1.91 | 0.91 | 0.50 | 0.82 | 3.20 | 2.29 |
| 200–250 um | 5.54 | 1.20 | 1.16 | 1.07 | 0.55 | 1.24 | 1.11 | 0.36 | 0.75 | 0.94 | 1.39 |
| 250–300 um | 3.33 | 0.81 | 1.12 | 1.04 | 0.58 | 1.14 | 0.81 | 0.37 | 0.39 | 0.78 | 1.04 |
| >300 um | 9.82 | 2.36 | 3.18 | 3.04 | 1.70 | 3.44 | 2.25 | 1.05 | 1.35 | 2.36 | 3.05 |
| SUM | 100.0 | 100.0 | 100.01 | 100.01 | 99.78 | 100.0 | 100.01 | 99.99 | 100.0 | 100.19 | 100.0 |

[1]Catalyst particles containing 0.5 weight-% palladium (on a total catalyst composition weight basis).
[2]On a palladium weight basis (i.e., values given are percentages of the 0.5 weight-% palladium).
[3]0 μm indicates the exterior surface of the catalyst particle.

The results shown in the above examples clearly demonstrate that the present invention is well adapted to carry out the objects and attain the ends and advantages mentioned as well as those inherent therein. Reasonable variations, modifications and adaptations for various usages and conditions can be made within the scope of the disclosure and the appended claims, without departing from the scope of this invention.

What is claimed is:

1. A composition useful in selectively hydrogenating diolefins and alkynes to monoolefins consisting essentially of:
   (a) at least one palladium-containing material selected from the group consisting of palladium metal and palladium oxides,
   (b) at least one alkali metal iodide, and
   (c) at least one inorganic support material, wherein said composition comprises about 0.01 weight-% palladium to about 2 weight-% palladium (on a total catalyst composition weight basis) and about 0.02 weight-% alkali metal to about 10 weight-% alkali metal (on a total catalyst composition weight basis) with said palladium concentrated in the skin of said composition.

2. A composition according to claim 1, wherein at least about 60 weight-% of said palladium (on a palladium weight basis) is concentrated in an area within about 150 microns of the exterior surface of said composition.

3. A composition according to claim 1, wherein said at least one inorganic support material is selected from the group consisting of alumina, silica, titania, zirconia, aluminosilicates, zinc aluminate, zinc titanate, and combinations thereof.

4. A composition according to claim 1, wherein said at least one alkali metal iodide is potassium iodide and said at least one inorganic support material is alumina.

5. A composition according to claim 1, wherein said at least one alkali metal iodide is potassium iodide and said at least one inorganic support material is zinc aluminate or zinc titanate.

6. A composition according to claim 1, comprising about 0.05 weight-% palladium to about 1 weight-% palladium (on a total catalyst composition weight basis) and about 0.05 weight-% alkali metal to about 5 weight-% alkali metal (on a total catalyst composition weight basis) with at least about 50 weight-% of said palladium (on a palladium weight basis) concentrated in an area within about 100 microns of the exterior surface of said composition and said composition having a surface area of about 1 m$^2$/g to about 200 m$^2$/g.

7. A composition according to claim 1, wherein
said at least one alkali metal iodide is potassium iodide,
said at least one inorganic support material is selected from the group consisting of alumina, silica, titania, zirconia, aluminosilicates, zinc aluminate, zinc titanate, and combinations thereof, and
said composition having a surface area of about 1 m$^2$/g to about 200 m$^2$/g.

8. A composition according to claim 7, comprising about 0.05 weight-% palladium to about 1 weight-% palladium (on a total catalyst composition weight basis) and about 0.05 weight-% potassium to about 5 weight-% potassium (on a total catalyst composition weight basis) with at least about 50 weight-% of said palladium (on a palladium weight basis) concentrated in an area within about 100 microns of the exterior surface of said composition and said surface area is about 5 m$^2$/g to about 100 m$^2$/g.

9. A composition according to claim 8, wherein said inorganic support material is alumina.

10. A composition according to claim 8, wherein said inorganic support material is zinc aluminate or zinc titanate.

11. A composition according to claim 1, having been prepared by a process consisting essentially of the steps of:
(i) contacting a material consisting essentially of component (a) and component (c) with a solution of at least one alkali metal iodide to obtain an alkali metal iodide-impregnated material,
(ii) drying said alkali metal iodide-impregnated material to obtain a dried material, and
(iii) heating said dried material in a non-oxidizing gas atmosphere at a temperature of about 300° C. to about 600° C. for a time period of about 0.2 hour to about 20 hours.

12. A composition according to claim 11, wherein said component (c) is alumina and said at least one alkali metal iodide is potassium iodide.

13. A composition according to claim 11, wherein said component (c) is zinc aluminate or zinc titanate and said at least one alkali metal iodide is potassium iodide.

14. A composition according to claim 1, having been prepared by a process comprising the steps of:
(i) contacting a material consisting essentially of component (a) and component (c) with a solution of at least one alkali metal iodide to obtain an alkali metal iodide-impregnated material,
(ii) drying said alkali metal iodide-impregnated material to obtain a dried material,
(iii) heating said dried material in a non-oxidizing gas atmosphere at a temperature of about 300° C. to about 600° C. for a time period of about 0.2 hour to about 20 hours to obtain a heated material, and
(iv) contacting said heated material with at least one sulfur-containing compound at a temperature of about 20° C. to about 25° C. for a time period of about 5 hours to about 20 hours.

15. A composition according to claim 14, wherein said at least one sulfur-containing compound is selected from the group consisting of sulfides, disulfides, mercaptans, mercaptides, thiophenes, thiophanes, thiophenols, benzothiophenes, dibenzothiophenes and combinations thereof.

16. A composition according to claim 14, wherein said at least one sulfur-containing compound is thiophene.

17. A composition according to claim 14, wherein said component (c) is alumina and said at least one alkali metal iodide is potassium iodide.

18. A composition according to claim 14, wherein said component (c) is zinc aluminate or zinc titanate and said at least one alkali metal iodide is potassium iodide.

19. A composition according to claim 1, having been prepared by a process comprising the steps of:
(i) contacting a material consisting essentially of component (a) and component (c) with a solution of at least one alkali metal iodate to obtain an alkali metal iodate-impregnated material,
(ii) drying said alkali metal iodate-impregnated material to obtain a dried material, and
(iii) heating said dried material in a reducing gas at a temperature of about 200° C. to about 600° C. for a time period of about 0.2 hour to about 20 hours, so as to convert said at least one alkali metal iodate to at least one alkali metal iodide.

20. A composition according to claim 19; wherein said component (c) is alumina and said at least one alkali metal iodate is potassium iodate.

21. A composition according to claim 19, wherein said component (c) is zinc aluminate or zinc titanate and said at least one alkali metal iodate is potassium iodate.

22. A process for making a composition useful in selectively hydrogenating diolefins and alkynes to monoolefins, said process consisting essentially of the steps of:
(i) contacting a material consisting essentially of
at least one palladium-containing material selected from the group consisting of palladium metal and palladium oxides, and
at least one inorganic support material, with a solution of at least one alkali metal iodide to obtain an alkali metal iodide-impregnated material,
(ii) drying said alkali metal iodide-impregnated material to obtain a dried material, and
(iii) heating said dried material in a non-oxidizing gas atmosphere at a temperature of about 300° C. to about 600° C. for a time period of about 0.2 hour to about 20 hours.

23. A process according to claim 22, wherein said at least one inorganic support material is alumina and said at least one alkali metal iodide is potassium iodide.

24. A process according to claim 22, wherein said at least one inorganic support material is zinc aluminate or zinc titanate and said at least one alkali metal iodide is potassium iodide.

25. A process for making a composition useful in selectively hydrogenating diolefins and alkynes to monoolefins, said process comprising the steps of:
(i) contacting a material consisting essentially of
at least one palladium-containing material selected from the group consisting of palladium metal and palladium oxides, and
at least one inorganic support material, with a solution of at least one alkali metal iodide to obtain an alkali metal iodide-impregnated material, (ii) drying said alkali metal iodide-impregnated material to obtain a dried material, (iii) heating said dried material in a non-oxidizing gas atmosphere at a temperature of about 300° C. to about 600° C. for a time period of about 0.2 hour to about 20 hours to obtain a heated material, and (iv) contacting said heated material with at least one sulfur-containing compound at a temperature of about 20° C. to about 25° C. for a time period of about 5 hours to about 20 hours.

26. A process according to claim 25, wherein said at least one sulfur-containing compound is selected from the group consisting of sulfides, disulfides, mercaptans, mercaptides, thiophenes, thiophanes, thiophenols, benzothiophenes, dibenzothiophenes and combinations thereof.

27. A process according to claim 25, wherein said at least one sulfur-containing compound is thiophene.

28. A process according to claim 25, wherein said at least one inorganic support material is alumina and said at least one alkali metal iodide is potassium iodide.

29. A process according to claim 25, wherein said at least one inorganic support material is zinc aluminate or zinc titanate and said at least one alkali metal iodide is potassium iodide.

30. A process for making a composition useful in selectively hydrogenating diolefins and alkynes to monoolefins, said process comprising the steps of:

(i) contacting a material consisting essentially of
   at least one palladium-containing material selected from the group consisting of palladium metal and palladium oxides, and
   at least one inorganic support material, with a solution of at least one alkali metal iodate to obtain an alkali metal iodate-impregnated material, (ii) drying said alkali metal iodate-impregnated material to obtain a dried material, and (iii) heating said dried material in a reducing gas at a temperature of about 200° C. to about 600° C. for a time period of about 0.2 hour to about 20 hours, so as to convert said at least one alkali metal iodate to at least one alkali metal iodide.

31. A process according to claim 30, wherein said at least one inorganic support material is alumina and said at least one alkali metal iodate is potassium iodate.

32. A process according to claim 30, wherein said at least one inorganic support material is zinc aluminate or zinc titanate and said at least one alkali metal iodate is potassium iodate.

33. A product prepared by the process of claim 22.
34. A product prepared by the process of claim 23.
35. A product prepared by the process of claim 24.
36. A product prepared by the process of claim 25.
37. A product prepared by the process of claim 26.
38. A product prepared by the process of claim 27.
39. A product prepared by the process of claim 28.
40. A product prepared by the process of claim 29.
41. A product prepared by the process of claim 30.
42. A product prepared by the process of claim 31.
43. A product prepared by the process of claim 32.

44. A composition useful in selectively hydrogenating diolefins and alkynes to monoolefins consisting essentially of:
   about 0.05 weight-% palladium to about 1 weight-% palladium (on a total catalyst composition weight basis),
   about 0.05 weight-% potassium in potassium iodide to about 5 weight-% potassium in potassium iodide (on a total catalyst composition weight basis), and
   at least one inorganic support material selected from the group consisting of alumina, silica, titania, zirconia, aluminosilicates, zinc aluminate, zinc titanate, and combinations thereof, wherein
   at least about 50 weight-% of said palladium (on a palladium weight basis) is concentrated in an area within about 100 microns of the exterior surface of said composition, and
   said composition having been heated in a non-oxidizing gas atmosphere at a temperature of about 300° C. to about 600° C. for a time period of about 0.2 hour to about 20 hours.

45. A composition according to claim 44, wherein said composition has a surface area of about 1 $m^2/g$ to about 200 $m^2/g$.

46. A composition useful in selectively hydrogenating diolefins and alkynes to monoolefins consisting essentially of:
   about 0.05 weight-% palladium to about 1 weight-% palladium (on a total catalyst composition weight basis),
   about 0.05 weight-% potassium in potassium iodate to about 5 weight-% potassium in potassium iodate (on a total catalyst composition weight basis), and
   at least one inorganic support material selected from the group consisting of alumina, silica, titania, zirconia, aluminosilicates, zinc aluminate, zinc titanate, and combinations thereof, wherein
   at least about 50 weight-% of said palladium (on a palladium weight basis) is concentrated in an area within about 100 microns of the exterior surface of said composition, and
   said composition having been heated in a reducing gas atmosphere at a temperature of about 200° C. to about 600° C. for a time period of about 0.2 hour to about 20 hours, so as to convert said at least one alkali metal iodate to at least one alkali metal iodide.

47. A composition according to claim 46, wherein said composition has a surface area of about 1 $m^2/g$ to about 200 $m^2/g$.

48. A process comprising contacting a fluid which comprises a highly unsaturated hydrocarbon, in the presence of hydrogen, with the composition of claim 1, under reaction conditions effective to convert said highly unsaturated hydrocarbon to a less unsaturated hydrocarbon.

49. A process comprising contacting a fluid which comprises a highly unsaturated hydrocarbon, in the presence of hydrogen, with the composition of claim 2, under reaction conditions effective to convert said highly unsaturated hydrocarbon to a less unsaturated hydrocarbon.

50. A process comprising contacting a fluid which comprises a highly unsaturated hydrocarbon, in the presence of hydrogen, with the composition of claim 3, under reaction conditions effective to convert said highly unsaturated hydrocarbon to a less unsaturated hydrocarbon.

51. A process comprising contacting a fluid which comprises a highly unsaturated hydrocarbon, in the presence of hydrogen, with the composition of claim 4, under reaction conditions effective to convert said highly unsaturated hydrocarbon to a less unsaturated hydrocarbon.

52. A process comprising contacting a fluid which comprises a highly unsaturated hydrocarbon, in the presence of hydrogen, with the composition of claim 5, under reaction conditions effective to convert said highly unsaturated hydrocarbon to a less unsaturated hydrocarbon.

53. A process comprising contacting a fluid which comprises a highly unsaturated hydrocarbon, in the presence of hydrogen, with the composition of claim 6 under reaction conditions effective to convert said highly unsaturated hydrocarbon to a less unsaturated hydrocarbon.

54. A process comprising contacting a fluid which comprises a highly unsaturated hydrocarbon, in the presence of hydrogen, with the composition of claim 33, under reaction conditions effective to convert said highly unsaturated hydrocarbon to a less unsaturated hydrocarbon.

55. A process comprising contacting a fluid which comprises a highly unsaturated hydrocarbon, in the presence of hydrogen, with the composition of claim 36, under reaction conditions effective to convert said highly unsaturated hydrocarbon to a less unsaturated hydrocarbon.

56. A process comprising contacting a fluid which comprises a highly unsaturated hydrocarbon, in the presence of hydrogen, with the composition of claim 41, under reaction conditions effective to convert said highly unsaturated hydrocarbon to a less unsaturated hydrocarbon.

57. A process according to claim 48, wherein said fluid further comprises an alkene.

58. A process according to claim 57, wherein said alkene is selected from the group consisting of ethylene, propylene, butenes, and combinations thereof.

59. A process according to claim 58, wherein said alkene is ethylene.

60. A process according to claim 59, wherein said highly unsaturated hydrocarbon is selected from the group consisting of diolefins, alkynes, and combinations thereof.

61. A process according to claim 60 wherein said diolefin is selected from the group consisting of propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and combinations thereof.

62. A process according to claim 61, wherein said diolefin is selected from the group consisting of propadiene, 1,3-butadiene, 1,3-pentadiene, 1,4-pentadiene, isoprene, 1,3-cyclopentadienes, dicyclopentadiene, and combinations thereof.

63. A process according to claim 62, wherein said alkyne is selected from the group consisting of acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and combinations thereof.

64. A process according to claim 63, wherein said alkyne is acetylene.

65. A process according to claim 64, wherein said fluid further comprises 50 to 99 weight % aromatic hydrocarbons.

66. A process according to claim 65, wherein said reaction conditions comprise a temperature in the range of from about 10° C. to about 300° C., a pressure in the range of from about 15 psig to about 2,000 psig, a liquid hourly space velocity of said fluid in the range of from about 0.5 liter of said fluid per liter of said composition per hour to about 100 liters of said fluid per liter of said composition per hour, and about 1 mole of hydrogen to about 10 moles of hydrogen are employed for each mole of said highly unsaturated hydrocarbon present in said fluid.

\* \* \* \* \*